United States Patent
Hubner et al.

(10) Patent No.: US 7,048,237 B2
(45) Date of Patent: May 23, 2006

(54) MOUNTING ASSEMBLY FOR A DENTAL X-RAY SYSTEM

(75) Inventors: Henry Hubner, Amityville, NJ (US); Walter Gross, Massapequa, NY (US)

(73) Assignee: Air Techniques, Inc., Hicksville, NY (US)

( * ) Notice: Subject to any disclaimer, the term of this patent is extended or adjusted under 35 U.S.C. 154(b) by 117 days.

(21) Appl. No.: 10/817,474

(22) Filed: Apr. 2, 2004

(65) Prior Publication Data

US 2005/0001112 A1 Jan. 6, 2005

Related U.S. Application Data

(60) Provisional application No. 60/461,034, filed on Apr. 8, 2003.

(51) Int. Cl.
*F21V 21/00* (2006.01)

(52) U.S. Cl. .................................. 248/121; 248/218.4

(58) Field of Classification Search ................ 248/121, 248/122.1, 125.7, 218.4, 288.11, 289.11, 248/291.1

See application file for complete search history.

(56) References Cited

U.S. PATENT DOCUMENTS

| | | | | |
|---|---|---|---|---|
| 3,662,961 A | * | 5/1972 | Hogrebe | 248/278.1 |
| 3,944,178 A | * | 3/1976 | Greenwood | 248/231.61 |
| 4,166,602 A | * | 9/1979 | Nilsen et al. | 248/280.11 |
| 4,447,031 A | * | 5/1984 | Souder et al. | 248/281.11 |
| 4,487,389 A | * | 12/1984 | Ziegler | 248/282.1 |
| 4,501,557 A | * | 2/1985 | Tamura et al. | 433/79 |
| 4,651,966 A | * | 3/1987 | Suzuki | 248/674 |
| 4,953,821 A | * | 9/1990 | Reuter et al. | 248/281.11 |
| 5,743,503 A | * | 4/1998 | Voeller et al. | 248/284.1 |
| 6,179,263 B1 | * | 1/2001 | Rosen et al. | 248/278.1 |
| 6,769,657 B1 | * | 8/2004 | Huang | 248/278.1 |
| 6,793,187 B1 | * | 9/2004 | McGee | 248/289.11 |
| 2004/0251389 A1 | * | 12/2004 | Oddsen | 248/279.1 |

* cited by examiner

*Primary Examiner*—Anita M. King
(74) *Attorney, Agent, or Firm*—Clifford G. Frayne; Louis E. Marn

(57) ABSTRACT

These and other objects of the present invention are achieved by an improved mounting assembly for a dental x-ray assembly comprised of a base plate member having outwardly-extending wall portions defining a U-shaped chamber along a longitudinal axis thereof and having upper threaded orifices and lower threaded orifices having axis perpendicular to the longitudinal axis of the base plate member and wherein a bearing block member is mounted with the U-shaped chamber for rotation by screw members threaded within the upper threaded orifices after mounting of the base plate member to a vertical support member in a vertical plane in a plane perpendicular to the vertical support member and wherein the block member is secured in the base plate member by locking means disposed in a lower threaded orifice once the bearing block is adjusted to a point eliminating any swinging of the dental x-ray assembly.

3 Claims, 3 Drawing Sheets

MOUNTING ASSEMBLY FOR A DENTAL X-RAY SYSTEM

RELATED APPLICATIONS

Applicant claims the benefit of provisional application Ser. No. 60/461,034, filed Apr. 8, 2003.

BACKGROUND OF THE INVENTION

1. Field of the Invention

This invention relates to a dental x-ray assembly system, and more particularly to a mounting assembly for a dental x-ray assembly system permitting of true vertical positioning thereof.

2. Description of the Prior Art

In dental operatories, a dental x-ray system is generally cantileverly positioned by a vertically-dispose shaft member in a mounting frame or bracket mounted to a vertical support member, such as a wall. The dental x-ray assembly includes a horizontally-disposed extension arm member mounted to the vertically-disposed shaft member disposed for rotation in the mounting assembly. At an end of the horizontally-disposed extension arm member remote from the mounting member, there is included vertically-disposed inner and outer positioning arm members articularly-mounted there between to each other. To the outer arm member, there is provided an x-ray tube head assembly extending downwardly from an end of the outer arm member for appropriately positioning an x-ray generating member of the x-ray tube head assembly at a point proximate a patient's oral cavity to effect imaging of such preselect portion thereof.

In mounting of the x-ray dental assembly, it is critical to ensure that an axis of the shaft member is coincident with a vertical line generated by the intersection of vertical planes disposed at right angles to each other to eliminate swing of the x-ray dental assembly to a point of lowest potential energy. Consequently, to effect such a mounting, shims are used between the mounting member and the vertical support member in a trial and error manner to eliminate such swinging of the x-ray dental assembly.

OBJECTS OF THE INVENTION

It is an object of the present invention to provide a mounting assembly for a dental x-ray assembly obviating the problems of the prior art.

Another object of the present invention is to provide a mounting assembly for a dental x-ray assembly eliminating the use of shims in a trial and error manner for the mounting to a vertical support member.

Yet another object of the present invention is to provide a mounting assembly for a dental x-ray assembly permitting facile readjustment of the vertical axis of rotation of the x-ray assembly.

A still further object of the present invention is to provide for a novel method for mounting a fixed extension arm of a dental x-ray unit to the wall mount frame or bracket to insure that the fixed extension arm pivots in a horizontal plane perpendicular to the wall surface.

SUMMARY OF THE INVENTION

These and other objects of the present invention are achieved by an improved mounting assembly for a dental x-ray assembly comprised of a base plate member having outwardly-extending wall portions defining a U-shaped chamber along a longitudinal axis thereof and having upper threaded orifices and lower threaded orifices having axis perpendicular to the longitudinal axis of the base plate member and wherein a bearing block member is mounted with the U-shaped chamber for rotation by screw members threaded within the upper threaded orifices after mounting of the base plate member to a vertical support member in a vertical plane in a plane perpendicular to the vertical support member and wherein the block member is secured in the base plate member by locking means disposed in a lower threaded orifice once the bearing block is adjusted to a point eliminating any swinging of the dental x-ray assembly.

BRIEF DESCRIPTION OF THE DRAWINGS

These and other objects of the present invention will become apparent, particularly when taken in light of the following drawings wherein.

DETAILED DESCRIPTION OF THE INVENTION

Figure 1:
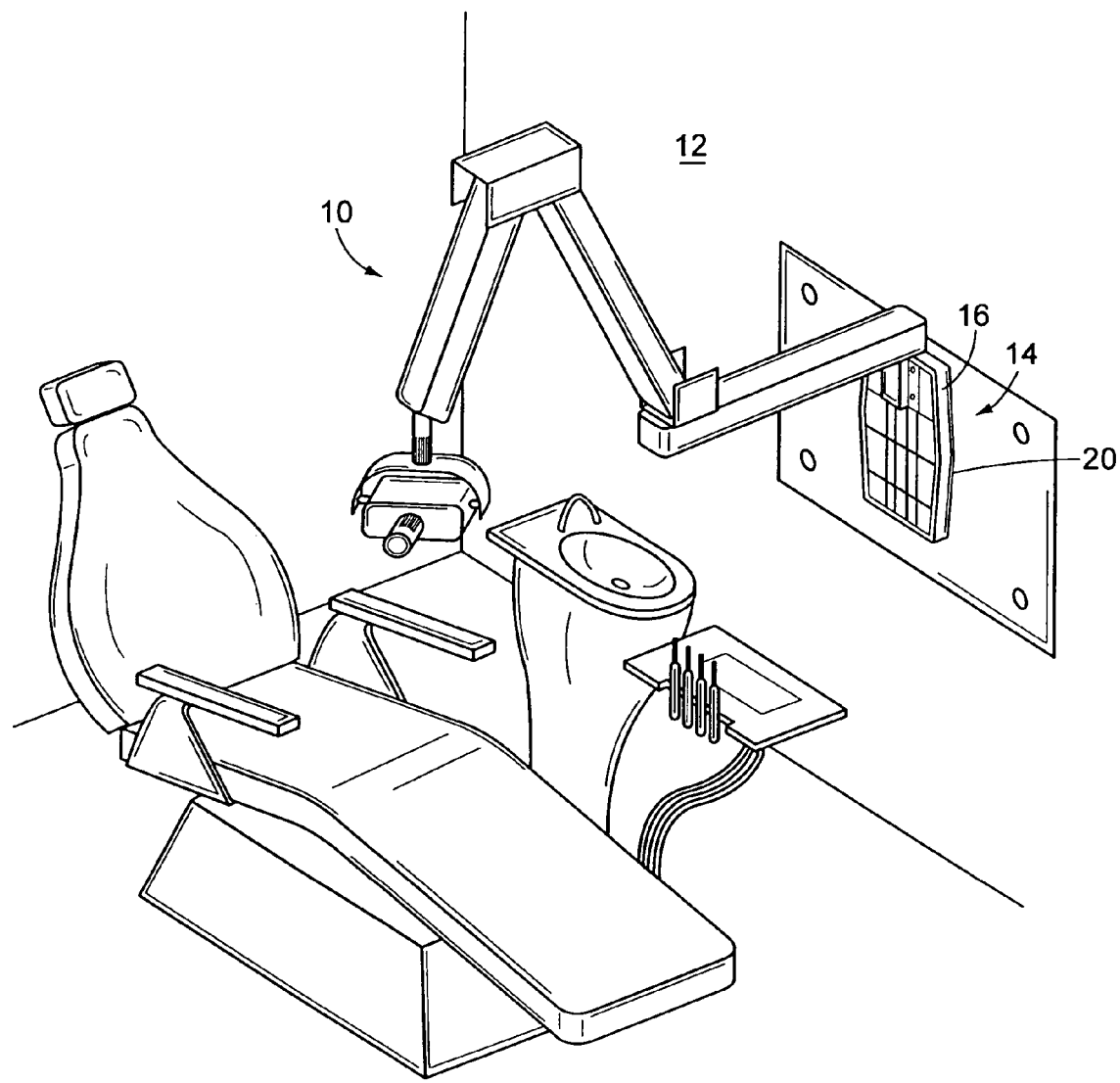
FIG. 1 is an elevational view of the mounting assembly of the present invention for a wall mounted dental x-ray in a dental operatory.

Referring to FIG. 1, there is illustrated a dental x-ray assembly generally indicated as 10 mounted to a vertical support member 12 by a mounting assembly generally indicated as 14 of the present invention disposed within a dental operatory. The mounting assembly 14 includes a cover member 16 including a control unit positioned on a base plate member 20 as more fully illustrated in FIGS. 2 and 3.

Figure 2:
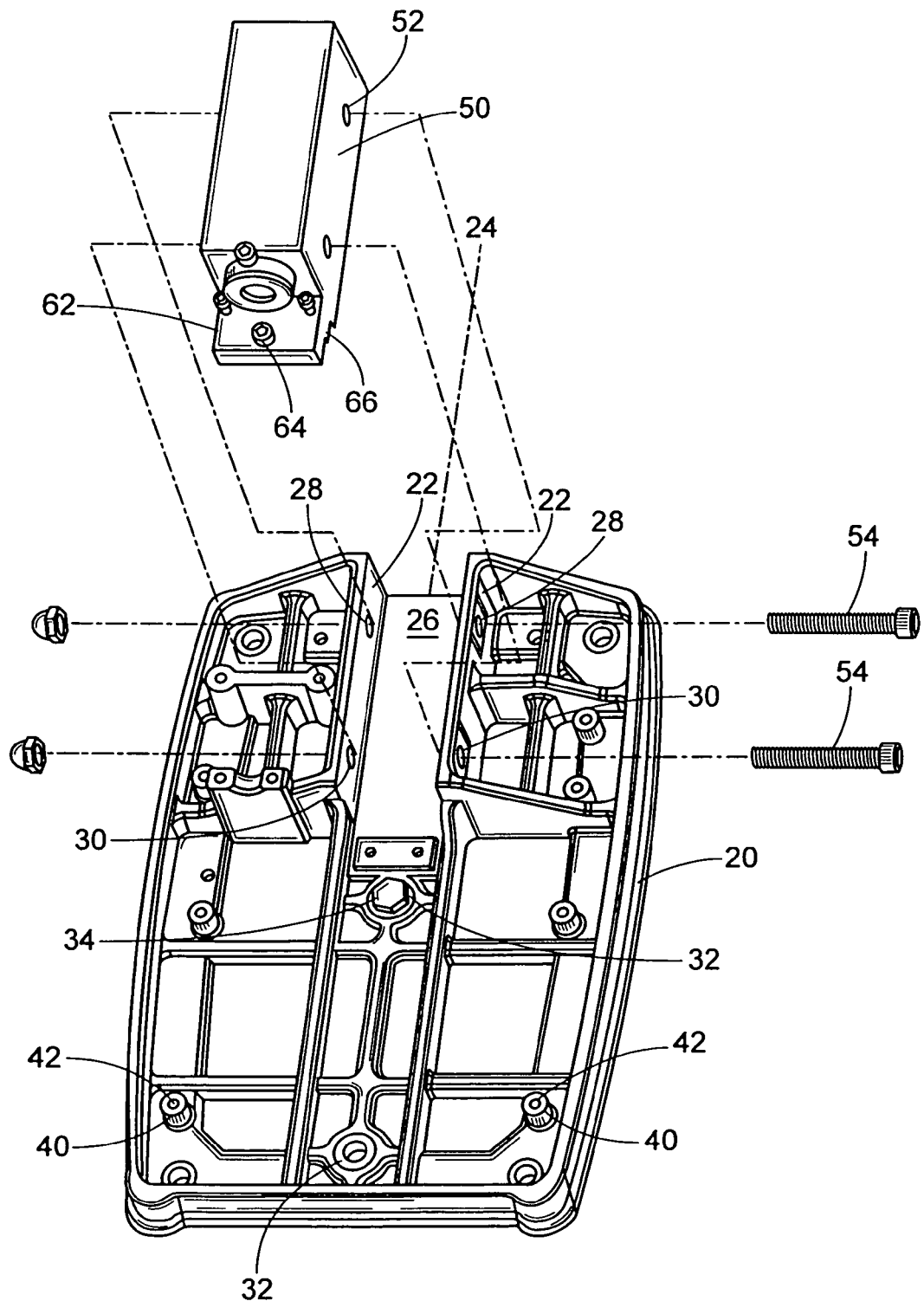
FIG. 2 is an exploded perspective view of the base plate member of the mounting assembly of the present invention.

Referring now to FIG. 2, the base plate member 20 having a planar back surface (not shown) is formed of a unitary construction to support the dental x-ray assembly 10, as more fully hereinafter discussed. At an upper end of the base plate member 20 there are formed paralleledly-disposed, outwardly extending wall sections 22 on either side of the longitudinal axis 24 of the base plate member 20 thereby defining a U-shaped chamber 26 there between. The wall sections 22 are formed with upper and lower paired orifices 28 and 30 as more fully hereafter discussed. The base plate member 20 is formed with a plurality of orifices 32 along the longitudinal axis 24 for fastening members 34, such as a screw for securing the plate member to a vertical support member, such as a wall 12 in FIG. 1. The base plate member 20 is formed with a plurality of outwardly extending, cylindrically-shaped trunk members 40 including threaded channels 42 for fastening screws 44 for mounting the cover plate 16 of the mounting assembly 14, again referring to FIG. 1.

Figure 3:
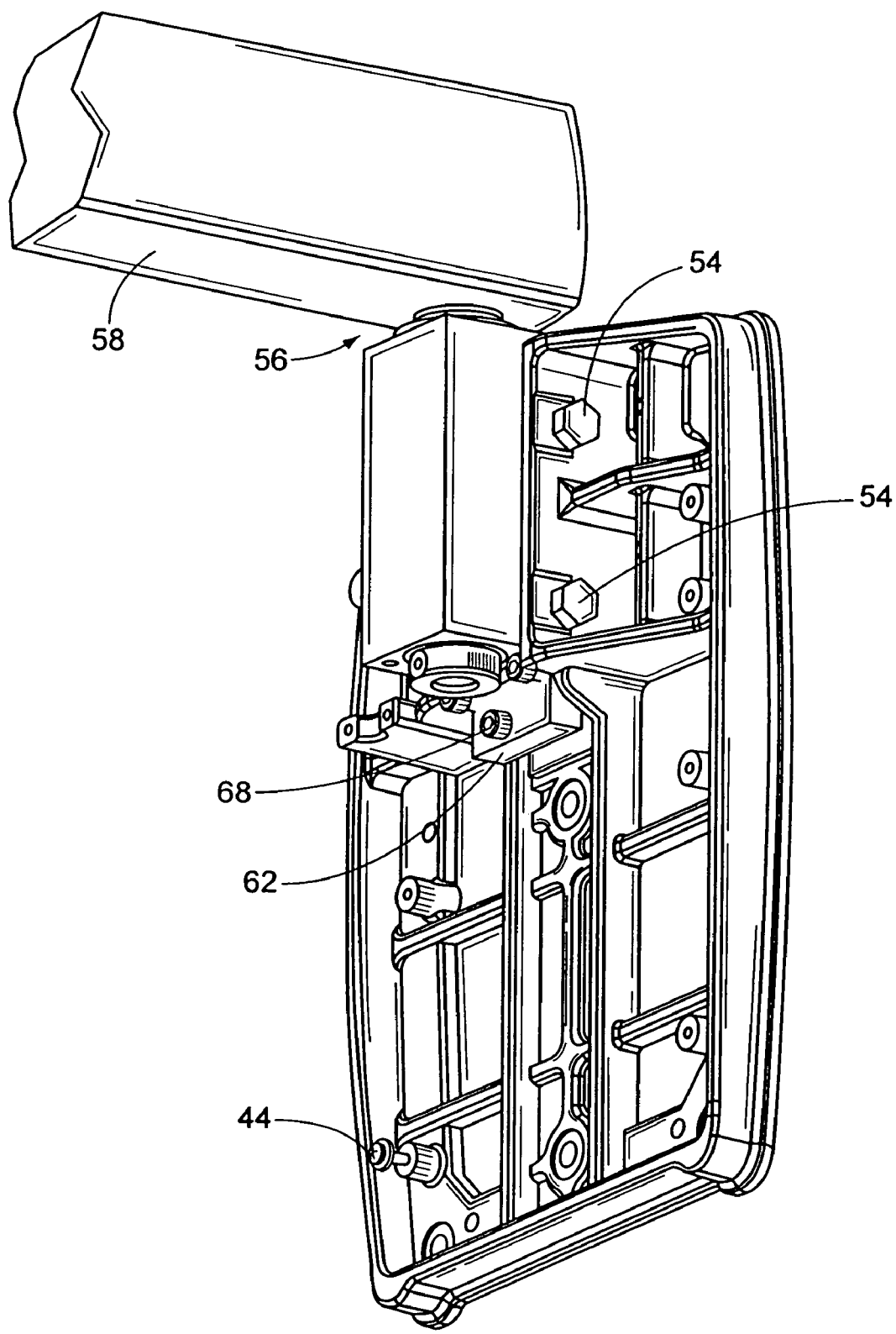
FIG. 3 is a perspective view of the mounting assembly of the present invention or a dental x-ray assembly.

The mounting assembly 14 includes an elongated bearing block member 50 referring again to FIG. 2, dimensioned for positioning in a U-shaped chamber 26 of the base plate member 20, including upper channels 52 for alignment with the upper paired threaded orifices 28 as more fully hereinafter discussed. The bearing block member 50 referring to FIGS. 2 and 3, is positioned within the U-shaped chamber 26 and is mounted for rotation by screw 54 extending through upper threaded orifice 28 of the base plate member 20 and the upper channel 52 of bearing block member 50. The bearing block member 50 is formed with a pivoting assembly generally indicated as 56 at the upper end thereof for connection with the extension arm 58 of the dental x-ray assembly 10.

The bearing block member 50 is formed with a downwardly extending leg portion 62 including a threaded orifice 64 and with stepped surface portions (not shown) for positioning a jack plate 66 between the stepped surface portions and the surface of the U-shaped chamber. A jack screw 68 is threaded through the threaded orifice 64 for cooperation with the jack plate 66 during final positioning of bearing block member 50 in the calibration to eliminate swing of the dental x-ray assembly 10 as hereinafter described.

In operation, the base plate member 20 is secured to the vertical support surface 12 whereby the longitudinal axis thereof is in a vertical plane perpendicular to a plane of the vertical support surface 12. Whereupon the bearing block member 50 is positioned with the U-shaped chamber 26 and the screws 54 threaded into the threaded orifices 28 in a manner to permit the bearing block member 50 to rotate about an axis formed by the axis of the orifices 28. The jack plate 66 is positioned in a stepped portion of the bearing block member 50 with the jack screw 68 being positioned and adjustable to the point where axis of the bearing block member is in a vertical plane perpendicular to the longitudinal axis of the base plate member 20. Thus, the axis of the bearing block member 50 should be coincidental with a line generated by vertical planes disposed at right angles to each other. Thereafter, locking bolts 54 are threaded with the threaded orifice 30 of the base plate 20 to a point where the bearing block is secured in the position eliminating any swinging of the dental x-ray assembly.

While the present invention has been described with respect to the exemplary embodiments thereof, it will be recognized by those of ordinary skill in the art that many modifications or changes can be achieved without departing from the spirit and scope of the invention. Therefore it is manifestly intended that the invention be limited only by the scope of the claims and the equivalence thereof.

What is claimed is:

1. A mounting assembly for a dental x-ray assembly, which comprises:

a base plate member formed with outwardly-extending wall portions defining a U-shaped chamber about a longitudinal axis thereof and including upper and lower cooperating threaded orifices, said base plate member formed with a plurality of orifices for receiving means disposed along said longitudinal axis of said base plate member for mounting said base plate member on a vertical support member; and an elongated bearing block member rectangular in cross section disposed within said U-shaped chamber of said base plate member, said elongated bearing block member is formed with a downwardly-extending leg portion formed with a threaded orifice and wherein a surface of said elongated bearing block member facing said U-shaped chamber is formed with stepped surface portions, said elongated bearing block member having upper orifices for alignment with and in rotating relationship to said upper cooperating threaded orifice by threaded members, said elongated bearing block member secured within said U-shaped chamber of said base plate member by securing means positioned within said lower cooperating threaded orifices once non-swinging positioning is achieved of said dental x-ray assembly with respect to said base plate member, said elongated bearing block member having support means for a support member of said dental x-ray assembly.

2. The mounting assembly for a dental x-ray assembly as defined in claim 1 and further including a jack plate member positioned between said stepped surfaces of said elongated bearing block member and a bottom surface of said U-shaped chamber of said base plate member and further including a securing means threaded into said threaded orifice of said leg downwardly extending portion for securing said jack plate member between said elongated bearing block member and said base plate member.

3. The mounting assembly for a dental x-ray assembly as defined in claim 1 wherein said base plate member is formed with a plurality of raised bosses having threaded chambers for positioning and securing a cover plate member of said dental x-ray assembly.

* * * * *